US010973735B2

(12) United States Patent
Silver et al.

(10) Patent No.: US 10,973,735 B2
(45) Date of Patent: Apr. 13, 2021

(54) CHEST COMPRESSION DEVICES FOR AUGMENTED CPR

(71) Applicant: ZOLL Medical Corporation, Chelmsford, MA (US)

(72) Inventors: Annemarie E. Silver, Chelmsford, MA (US); Guy R. Johnson, Chelmsford, MA (US); Gary A. Freeman, Chelmsford, MA (US); Ulrich R. Herken, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1261 days.

(21) Appl. No.: 15/142,886

(22) Filed: Apr. 29, 2016

(65) Prior Publication Data

US 2016/0317384 A1 Nov. 3, 2016

Related U.S. Application Data

(60) Provisional application No. 62/154,648, filed on Apr. 29, 2015.

(51) Int. Cl.
*A61H 31/00* (2006.01)
*A61N 1/39* (2006.01)

(52) U.S. Cl.
CPC ......... *A61H 31/005* (2013.01); *A61H 31/007* (2013.01); *A61H 31/008* (2013.01); *A61N 1/3937* (2013.01); *A61N 1/3968* (2013.01); *A61H 2031/002* (2013.01); *A61H 2031/003* (2013.01); *A61H 2201/1207* (2013.01); *A61H 2201/1253* (2013.01); *A61H 2201/1436* (2013.01); *A61H 2201/1445* (2013.01); *A61H 2201/1619* (2013.01); *A61H 2201/1645* (2013.01); *A61H 2201/5043* (2013.01); *A61H 2201/5048* (2013.01); *A61H 2201/5076* (2013.01); *A61H 2201/5079* (2013.01); *A61H 2201/5084* (2013.01); *A61H 2205/084* (2013.01); *A61H 2230/04* (2013.01)

(58) Field of Classification Search
CPC .................. A61H 31/00–008; A61H 2205/084
See application file for complete search history.

(56) References Cited

U.S. PATENT DOCUMENTS

| 443,204 A | 12/1890 | Davis |
| 651,962 A | 6/1900 | Boghean |
| 2,071,215 A | 2/1937 | Petersen |
| 2,486,667 A | 11/1949 | Meister |
| RE26,511 E | 12/1968 | Hewson |
| 3,568,078 A | 3/1971 | Pelchat |
| 4,424,806 A | 1/1984 | Newman et al. |
| 4,554,910 A | 11/1985 | Lally |
| 4,676,232 A | 6/1987 | Olsson et al. |
| 4,770,164 A | 9/1988 | Lach et al. |

(Continued)

OTHER PUBLICATIONS

Strohmenger, et al., Spectral Analysis of Ventricular Fibrillation and Closes-Chest Cardiopulmonary Resuscitation, 33 Resuscitation 155 (1996).

(Continued)

*Primary Examiner* — Rachel T Sippel
(74) *Attorney, Agent, or Firm* — ZOLL Medical Corporation

(57) ABSTRACT

Devices and methods for CPR chest compression with active decompression.

33 Claims, 13 Drawing Sheets

(56) References Cited

U.S. PATENT DOCUMENTS

| | | |
|---|---|---|
| 4,860,759 A | 8/1989 | Kahn et al. |
| 4,928,674 A | 5/1990 | Halperin et al. |
| 4,932,879 A | 6/1990 | Ingenito et al. |
| 4,987,783 A | 1/1991 | D'Antonio et al. |
| 4,989,611 A | 2/1991 | Zanetti et al. |
| 5,453,081 A | 9/1995 | Hansen |
| 5,490,820 A | 2/1996 | Schock et al. |
| 5,496,257 A | 3/1996 | Kelly |
| 5,704,365 A | 1/1998 | Albrecht et al. |
| 5,738,637 A | 4/1998 | Kelly et al. |
| 5,743,864 A | 4/1998 | Baldwin, II |
| 5,794,623 A | 8/1998 | Forbes |
| 5,831,164 A | 11/1998 | Reddi et al. |
| 5,844,482 A | 12/1998 | Guthrie et al. |
| 5,876,350 A | 3/1999 | Lo et al. |
| 5,957,856 A | 9/1999 | Weil et al. |
| 5,978,693 A | 11/1999 | Hamilton et al. |
| 6,013,041 A | 1/2000 | Leathers |
| 6,027,452 A | 2/2000 | Flaherty et al. |
| 6,090,056 A | 7/2000 | Bystrom et al. |
| 6,174,295 B1 | 1/2001 | Cantrell et al. |
| 6,179,793 B1 | 1/2001 | Rothman et al. |
| 6,301,964 B1 | 10/2001 | Fyfe et al. |
| 6,865,413 B2 | 3/2005 | Halperin et al. |
| 7,074,199 B2 | 7/2006 | Halperin et al. |
| 7,108,665 B2 | 9/2006 | Halperin et al. |
| 7,122,014 B2 | 10/2006 | Palazzolo et al. |
| 7,220,235 B2 | 5/2007 | Geheb et al. |
| 7,295,871 B2 | 11/2007 | Halperin et al. |
| 7,297,125 B2 | 11/2007 | Palmer et al. |
| 7,429,250 B2 | 9/2008 | Halperin et al. |
| 7,775,996 B2 | 8/2010 | Stromsnes |
| 8,002,720 B2 | 8/2011 | Hansen et al. |
| 8,535,251 B1 | 9/2013 | Rao |
| 2004/0162510 A1* | 8/2004 | Jayne ............... A61H 31/005 601/41 |
| 2007/0135739 A1 | 6/2007 | Halperin et al. |
| 2008/0097261 A1 | 4/2008 | Hansen et al. |
| 2008/0097534 A1 | 4/2008 | Myklebust et al. |
| 2010/0198118 A1 | 8/2010 | Itnati |
| 2012/0083720 A1 | 4/2012 | Centen et al. |
| 2012/0184882 A1 | 7/2012 | Totman et al. |
| 2012/0191014 A1 | 7/2012 | Fossan |
| 2014/0155792 A1* | 6/2014 | Karve ............... A61H 9/0078 601/41 |
| 2014/0171840 A1 | 6/2014 | Aelen et al. |
| 2016/0158082 A1* | 6/2016 | Gainor ............... A61G 7/075 5/690 |

OTHER PUBLICATIONS

Pinchak, et al., Chest Wall Acceleration and Force Measurements in Simulated Manual and Mechanical Cardiopulmonary Resuscitation, 16 Critical Care Medicine 151 (1988).

Pinchak, et al., Accelerometer Measurements in CPR, 37th ACEMB 32 (1984).

International Search Report and Written Opinion dated Jan. 29, 2015 from PCT Application US2014/063338.

* cited by examiner

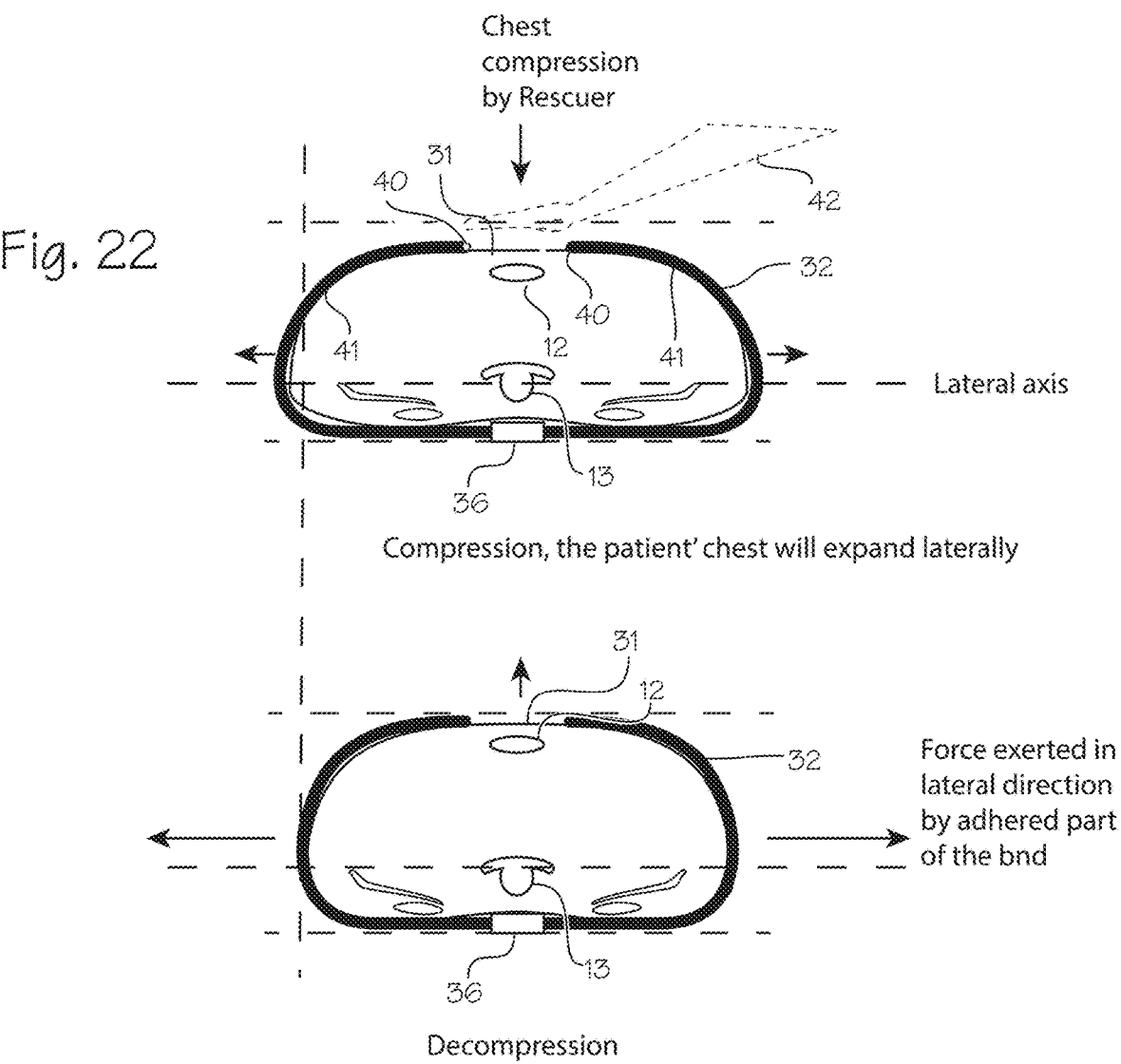

CHEST COMPRESSION DEVICES FOR AUGMENTED CPR

This application claims priority to U.S. Provisional Application 62/154,648, filed Apr. 29, 2015, which is hereby incorporated by reference in its entirety.

FIELD OF THE INVENTIONS

The inventions described below relate the field of CPR.

BACKGROUND OF THE INVENTIONS

Chest compressions provided as a component of cardiopulmonary resuscitation (CPR) should be accomplished at a consistent depth of about 2 inches, according to the CPR Guidelines 2010. This is difficult to accomplish, especially over a long course of CPR. Chest compression monitors, such as those used in ZOLL Medical Corporation's CPR D Padz® and Real CPR chest compression monitor, give real time feedback to a CPR provider, measuring the depth and rate of compressions achieved during CPR and providing immediate reports of achieved chest compression depth to the CPR provider. This helps the CPR provider achieve the desired compression depth and also helps the CPR provider realize when he is too fatigued to provider proper chest compressions. In use, the chest compression monitor is sandwiched between the chest of a cardiac arrest victim and the hands of a CPR provider during compressions. These chest compression monitors are free-floating, and can accurately measure chest compression depth without reference to any external reference or input. This is described in Halperin, et al., CPR Chest Compression Monitor, U.S. Pat. No. 6,390,996 (May 21, 2002), as well as Palazzolo, et al., Method of Determining Depth of Chest Compressions During CPR, U.S. Pat. No. 7,122,014 (Oct. 17, 2006). Nonetheless, these chest compression monitors can be augmented with reference sensors, to ensure or improve accuracy when chest compressions are performed on a patient that is coincidentally subject to gross vertical movements. For example, Palazzolo, et al., Method Of Determining Depth Of Chest Compressions During CPR, U.S. Pat. No. 7,122, 014 (Oct. 17, 2006) disclosed a system including a chest compression monitor disposed on the chest of a cardiac arrest victim and a reference sensor disposed elsewhere on the body of the cardiac arrest victim or a gurney supporting the cardiac arrest victim.

For adults, CPR chest compressions are delivered while the patient is supine, supported by a sufficiently rigid surface (a floor, gurney, or hospital bed). For infants, CRP chest compressions are provided with one of two methods. The preferred method is the two-thumb method, and entails grasping the infants thorax with both hands, placing both thumbs over the sternum (with the fingers supporting the back of the infant) and compressing the sternum with the thumbs. Another method, suggested for use by a lone rescuer, is referred to as the two-finger method, and entails compression of the infant's chest with two fingers placed over the inter-mammary line (superior to the xiphoid process). Compressions should be about 1.5 inches (3.8 cm) (one third of the thickness of the thorax of 4.5 inches (11.4 cm), which is rough estimate of infant chest thickness which is of course variable depending on the age of the infant patient). The chest should be released completely after each compression. According to the American Heart Association, the 2-thumb-encircling hands technique is preferred over the 2-finger technique because it produces higher coronary artery perfusion pressure, results more consistently in appropriate depth or force of compressions, and may generate higher systolic and diastolic pressures.

In another aspect of CPR, active compression-decompression CPR has been suggested as an adjunct to CPR. Active compression-decompression refers to compression techniques which include some mechanism for actively lifting the chest wall between compression down strokes, rather than merely relying on the natural resilience of the chest wall to expand the chest between compressions. Active decompression devices, such as proposed by Steen, Systems and Procedures for Treating Cardiac Arrest, U.S. Pat. No. 7,226,427 (Jun. 5, 2007), use a piston to compress the chest. The piston is driven up and down by a motor. A suction cup on the lower face of the piston is intended to pull the chest wall up with the piston. Active decompression is not yet recommended for pediatric use.

Voss, et al. (including Lurie), Guided Active Compression Cardiopulmonary Resuscitation Systems and Methods, U.S. Pat. No. 8,702,633 (Apr. 22, 2014) discloses a device to facilitate manual chest compressions, including a handle connected to the chest during use with an adhesive pad which can be used to provide active decompression by manually lifting the chest upward between compressions. Steen, Systems and Procedures for Treating Cardiac Arrest, U.S. Pat. No. 7,226,427 (Jun. 5, 2007) (Jolife) discloses a piston-based CPR chest compression device with a solid pad disposed on the bottom surface of a piston which is used to push downwardly to compress the chest. The bottom surface of the pad is adhesive, and adheres to the chest wall of the patient, which provides active decompression to pull the chest upward between compressions. To provide a compression cycle while using these systems, the CPR provider must push down on the patient's sternum to provide compression, and then pull the device upward to provide active decompression.

Each of these systems compresses the chest with a downward compression stroke, with a force applied in a posterior direction along the anterior-to-posterior axis of the chest. During manual CPR or piston-based CPR, downward force is applied to the sternum. During belt driven CPR, the forces applied over the anterior surface of the chest wall cause coincident flexion and rotation of the ribs (folding/collapsing inferiorly and closing clam-shell style in an adduction-like movement) as well as downward movement of the sternum.

Turning now to the mechanics of the human chest, the chest is known to naturally expand upon relaxation (for example, during respiration or chest release after compression), pivoting about a hinge point at the connection point between the vertebrae of the spine and the ribs. The head of each rib is the end that connects to the spine, and the ribs articulate about this connection during compression and subsequent release (and also during normal inhalation and exhalation). The shaft or body of each rib is the somewhat flattened portion that extends laterally from the head, out toward the axillary region, and then curves anteriorly and then medially to meet the sternum (presenting the rib shape known in human anatomy, which may be described as approximately C-shaped). The sternal end of the rib is the anterior termination of the rib, and the part that connects to the sternum, through the costal cartilage either directly (the true ribs 1-7) or indirectly through coastal cartilage of the ribs above them (false ribs 8-10). The sternal end of the rib is capable of articulating, or rotating, relative to the sternum.

During the release phase of each compression cycle, in the process of natural expansion, the ribs resiliently return toward their original condition expanding laterally (along the lateral or transverse axis) and also such that the sternal end moves upward (in an anterior direction away from the spine along the anterior-posterior axis) as well as in a superior direction (along the superior-inferior axis). The movement of the ribs outward and upward is referred to as the "bucket handle" movement and the motion of the ribs during natural chest expansion is referred to as the "pump handle" movement, as described in the literature.

The movement of the sternum, which is composed of the manubrium, body, and xiphoid process is also described in the literature, for example, as it undergoes upward expansion when breathing deeply. The manubrium is somewhat fixed to the first rib, whereas the body is more flexible around the 2nd to 7th rib. Thus, movement of the sternum can be described as hinge-like during deep inspiratory and relaxed expiratory phases. For extension, the extensor muscle group is the most active, with a motion range of approximately 20-25 degrees. The process of chest extension is also described in the literature, for example it is known that during extension the ribs move in the superior direction (along the superior-inferior axis). Thus, as described above, it is well known that during the natural expansion of the chest, whether during unaided release after chest compression or during respiration, the chest expands in multiple directions. Also, the sternum exhibits not only the posterior to anterior (downward to upward) trajectory, but also motion in the superior direction. Other parts of the chest also expand laterally. Thus there is a need for facilitating chest expansion during chest release in the process of performing chest compressions and/or decompressions that more closely resembles natural chest expansion.

SUMMARY

The devices and methods described below provide for chest compression monitoring during CPR provided to infant cardiac arrest victims, especially where compressions are provided with the two-thumb method. The device includes a chest compression monitor and a reference sensor mounted on the tips of an easily deformable open frame which fits around the infant's thorax. The open frame is place around the infant's thorax, with one sensor disposed on the compression point and one sensor disposed on the infant's back, and the CPR provider performs the two-thumb compression technique with one sensor trapped between his thumbs and the infant's chest, and the other sensor trapped between the rescuer's fingers and the infant's back. The device used to measure chest compression depth can be augmented to provide active decompression for infant cardiac arrest victims. The frame which holds the device may be resilient, such that it forcefully returns to an open position, and the tips of the frame may be adhesive, such that they adhere to the infants chest and back, such that upon each release by the CPR provider, the frame exerts a gently expansive force on the infant's thorax.

Additional devices and methods described below provide for an augmented release phase and/or active decompression during the release phase of chest compressions. These devices comprise one or more arcuate bands, comprising one or more resilient portions, capable of conforming to a patient's chest and transitioning between a compressed and uncompressed state. A part or all of the augmented release device may be adhered to the patient's chest. The devices augment and hasten the natural resilient expansion of the chest during chest release and thus provide beneficial active decompression forces.

10b which shows an augmented release device constructed from two arcuate bands and a spring component.

Figure 11:
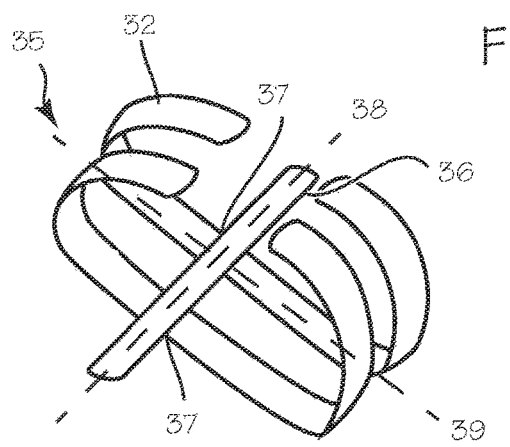

FIG. 11 shows an augmented release device in an open, large diameter configuration.

Figure 12:
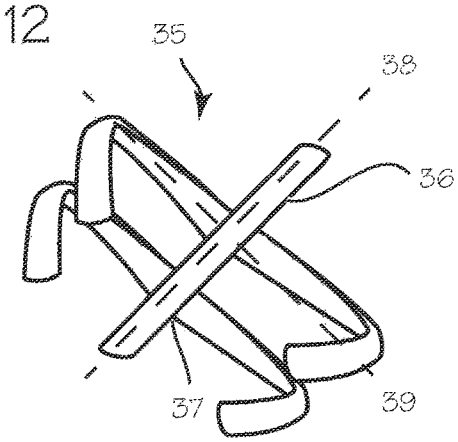

FIG. 12 shows the augmented release device of FIG. 11 in a compressed, small diameter configuration.

Figure 13:
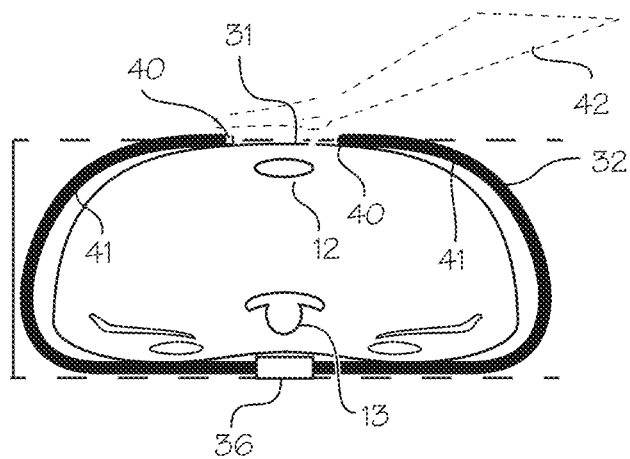

FIG. 13 shows a cross section of an augmented release device fitted about a patient.

Figure 14:
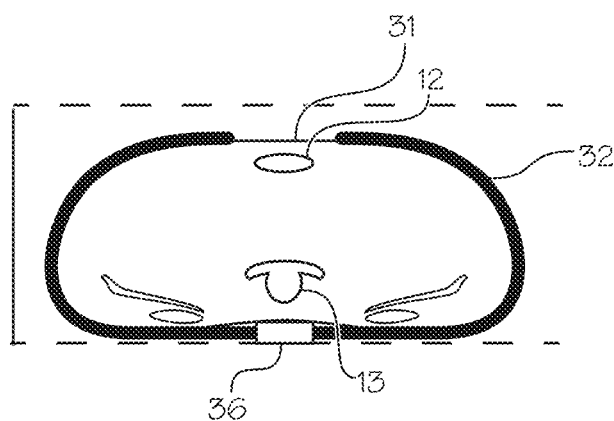

FIG. 14 shows a cross section of the augmented release device fitted about a patient, with arcuate bands conforming to the chest compressed.

Figure 15:
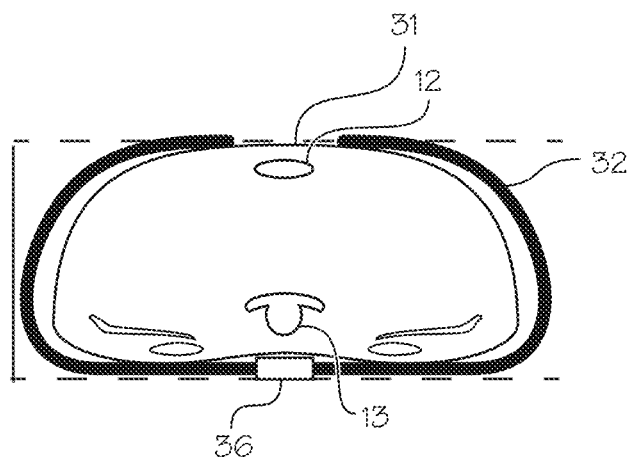

FIG. 15 shows a cross section of the augmented release device fitted about a patient, with arcuate bands conforming to the chest expanded during the release phase of the compression cycle.

Figure 16:
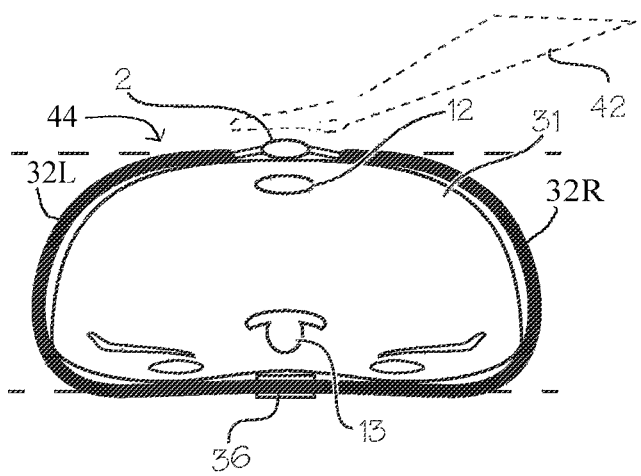

FIG. 16 shows an augmented release device fitted with a compression monitor.

Figure 17:
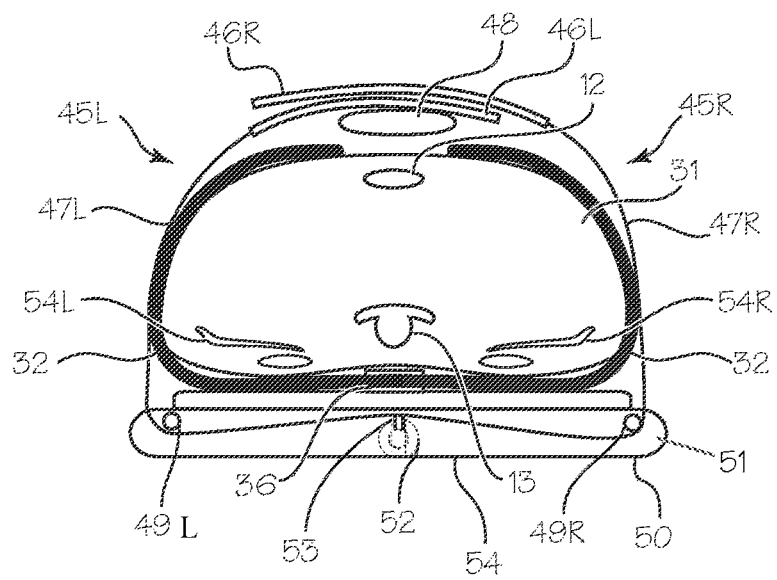

FIG. 17 shows an augmented release device combined with an automated chest compression device.

Figure 18:
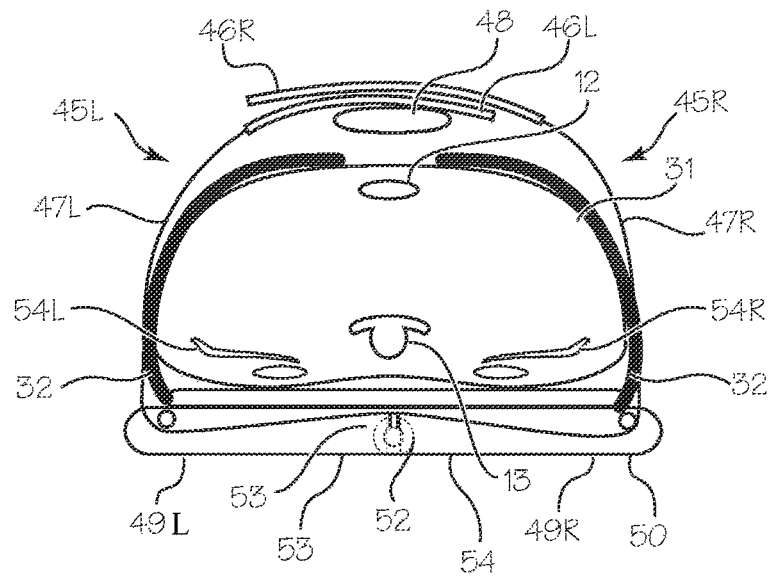

FIG. 18 shows an augmented release device combined with an automated chest compression device, with chest conforming portions arising from the housing of the chest compression device.

Figure 19:
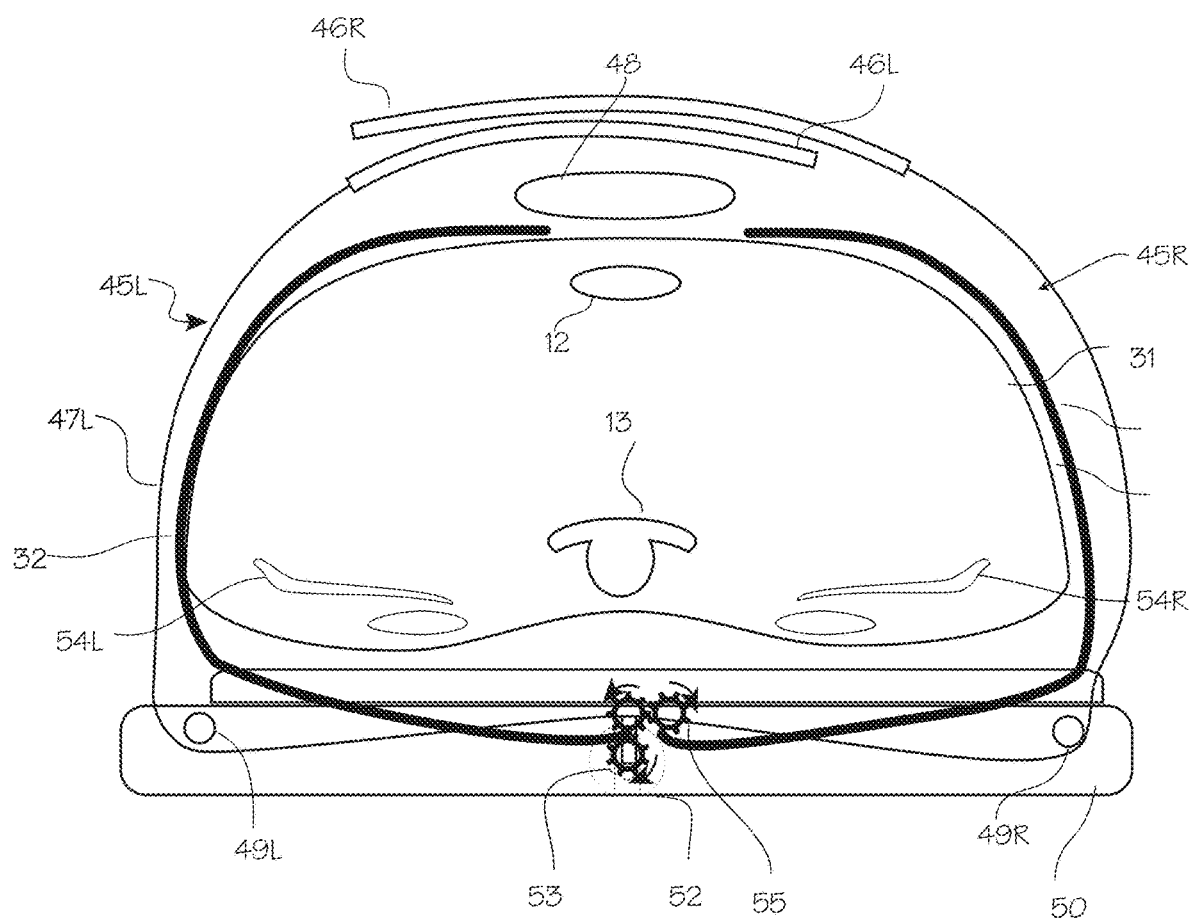

FIG. 19 illustrates an augmented release device in combination with an automated chest compression device in which the assembly is driven by a motor.

Figure 20A:
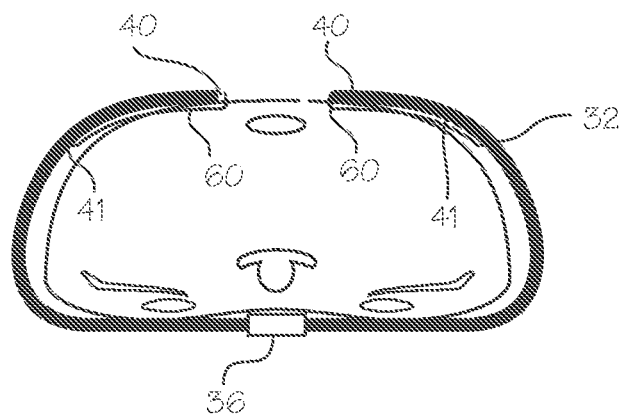
Figure 20B:
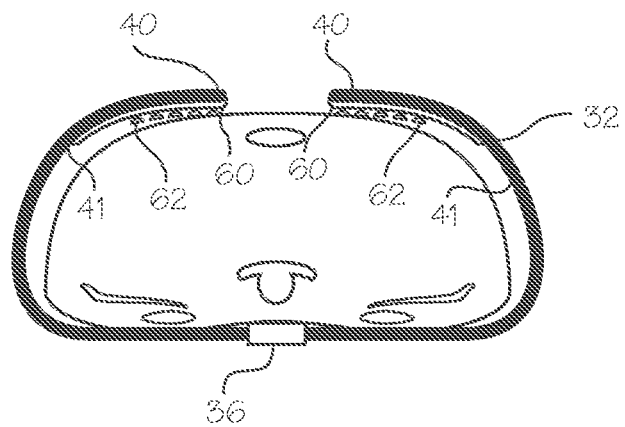

FIGS. 20a and 20b illustrate an augmented released device adhered at or near the sternum of the chest of a patient with adhesives, FIG. 20a, or suction cups, FIG. 20b.

Figure 21:
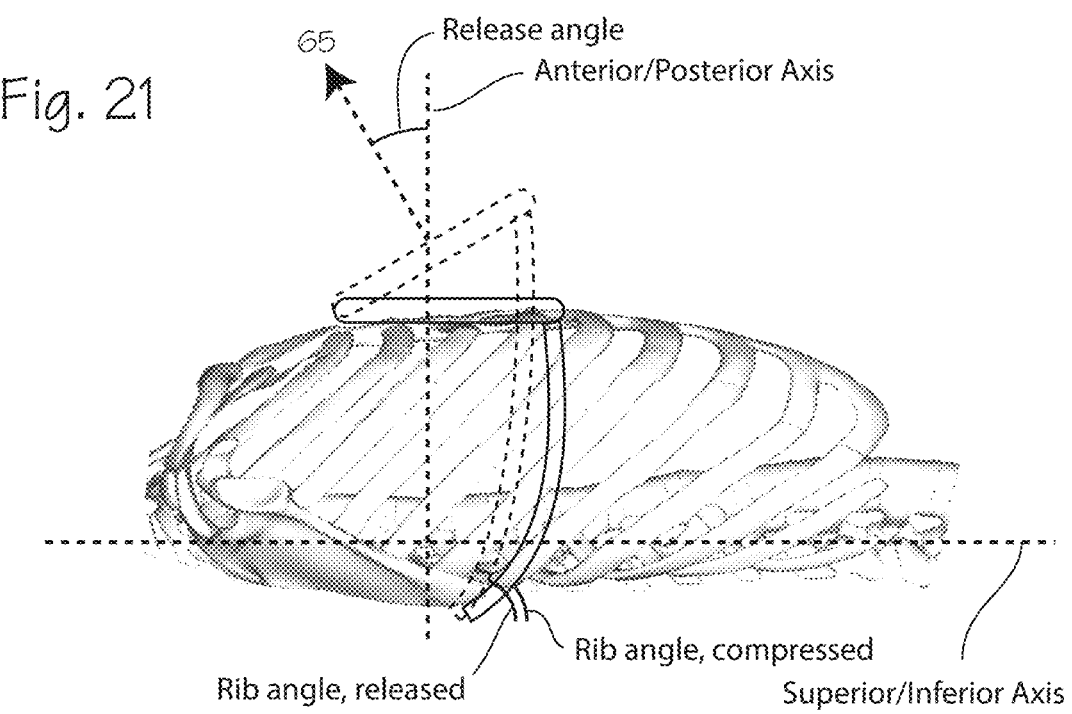

FIG. 21 illustrates the direction of the force vector of the force exerted by the augmented release device on the chest where the anterior ends are adhered to the chest of a patient above or near the sternum.

FIG. 22 illustrates the force exerted in the lateral directions on the sides of a patient's chest where the device is biased into an open configuration having a lateral diameter that is larger than the lateral diameter of the patient's chest.

DETAILED DESCRIPTION OF THE INVENTIONS

Figure 1:
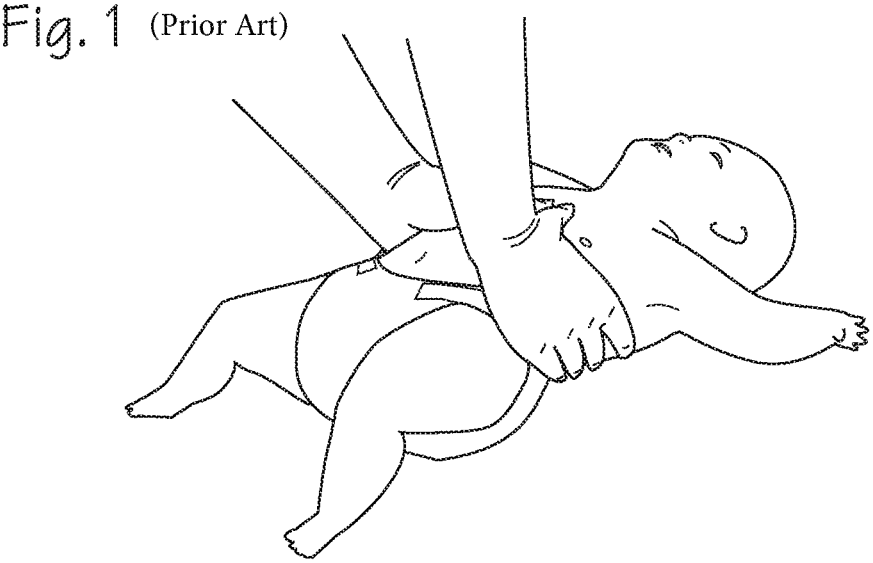
FIG. 1 illustrates the two-thumb technique for accomplishing CPR compressions on an infant.

FIG. 1 illustrates the two-thumb technique for accomplishing CPR compressions on an infant. The infant is shown supine, supported on a surface. A CPR provider has placed his hands around the infant's thorax, placing his thumbs over the infant's sternum with his fingers wrapping over the axillary area under the infant's arms and around the infant's back. In this method, the CPR provider squeezes the infant's thorax, with the thumbs pressing on the sternum, to push the sternum toward the spine. These compression should be accomplished at a rate of 100 compressions per minute and a depth of 1.5 inches (3.8 cm)(or about one-third of the total thickness of the thorax).

Figure 2:
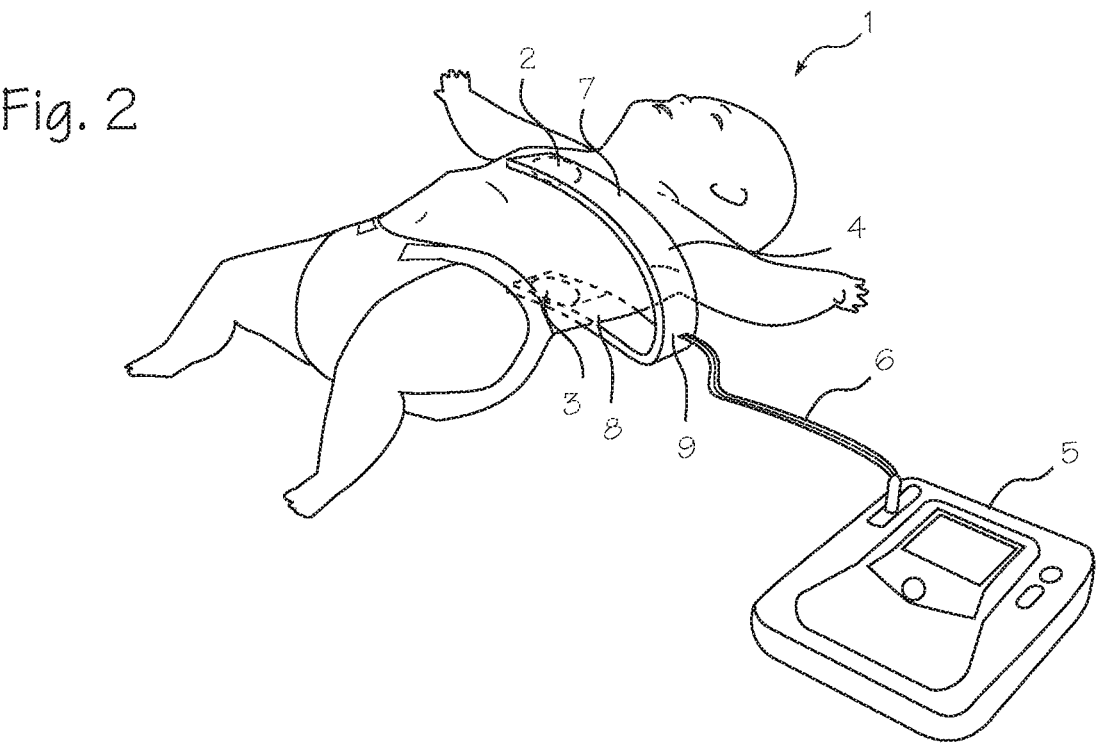
FIG. 2 illustrates placement of the new chest compression depth monitoring system on an infant cardiac arrest victim.

FIG. 2 illustrates placement of the new chest compression depth monitoring system on an infant cardiac arrest victim 1. The system includes a first sensor 2 located over the sternum and a second sensor 3 located on the back. These two sensors are mounted on a frame 4, which, as illustrated, is a U-shaped frame defining an open space which accommodate the infant. The sensors are mounted on the frame such that, with the frame disposed about the infant's thorax, the sensors may be properly located over the sternum and opposite the sternum on the infant's back. The sensors are operably connected to an automatic external defibrillator (AED) 5 through cable 6. The AED box 5 includes a control system, a display and speaker, and a defibrillator. The display and speaker are operable for providing visual or audio feedback to the CPR provider regarding the depth and rate of the compressions provided by the CPR provider, and comprise means for providing feedback to the CPR provider. The AED also includes an input device, such as a keyboard, soft-keys or touchscreen (which may also be used as the display). The control system (a computer) is programmed to interpret the acceleration signals to calculate compression depth and/or velocity (specifically, release velocity), and generate visual displays and/or audio prompts to be displayed or played to guide the CPR provider. (The control system also analyzes ECG signals obtained from ECG electrodes, not shown, to determine if defibrillating shock should be applied, and may prompt the user to apply shock or automatically operate the defibrillator to apply shock to the infant patient.) The control system can also be provided in a stand-alone device, without the defibrillator function. The control system comprises at least one processor and at least one memory including program code with the memory and computer program code configured with the processor to cause the system to perform the functions described throughout this specification.

Figure 3:
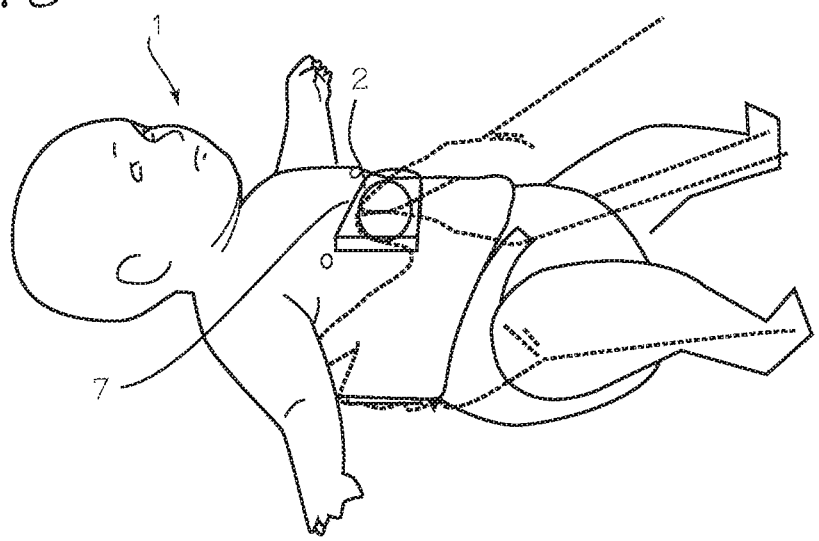
FIG. 3 illustrates the two-thumb technique for accomplishing CPR compressions on an infant while the system of FIG. 2 is installed on the infant.

FIG. 3 illustrates the two-thumb technique for accomplishing CPR compressions on an infant while the system of FIG. 2 is installed on the infant. As in FIG. 2, the frame 4 is disposed about the thorax of the infant, with the first sensor 2 disposed over the sternum of the infant and the second sensor 3 (see FIG. 2) disposed on or under the back of the infant. The rescuer is shown with his/her thumbs over the first sensor, trapping the first sensor between the rescuer's thumbs and the infant's sternum, and the fingers of both hands wrapped around the infant's thorax, preferably trapping the second sensor between the fingers of the rescuer and the back of the infant.

Figure 4:
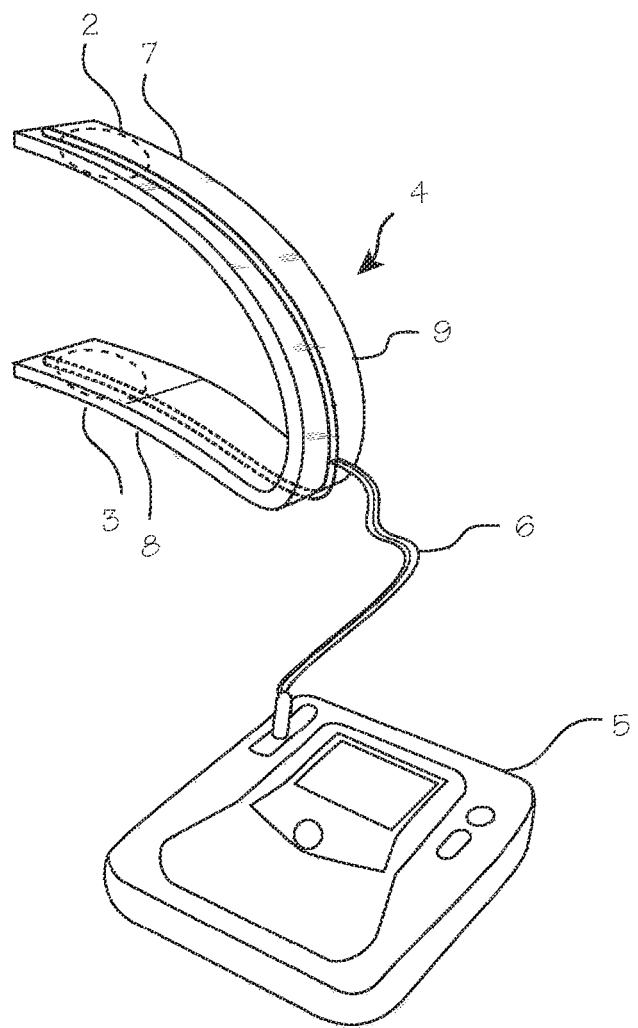
FIG. 4 illustrates the frame in isolation.

FIG. 4 illustrates the frame in isolation. The frame may take on many forms, and is illustrated as a U-shaped frame 4, comprising two laterally extending elements 7 and 8 joined by an arcuate segment 9. The sensors 2 and 3 are mounted near the tips 10 and 11 of extending elements, so that they can easily be located with the first sensor 2 disposed over the sternum of the infant and the second sensor 3 disposed on or under the back of the infant. The frame construction assures proper placement of the sensors on the anterior and posterior surface of the infant, so that motion signals from each sensor can be used to measure the chest wall motion induced by the CPR compressions accomplished by the CPR provider, taking into account any anterior/superior motions of the infants entire thorax attendant to the two-thumbs technique. The frame is preferably resilient and biased to an open configuration (as large or larger than the thickness of the infant's chest), such that after each compression, it resiliently returns to an open position, but may instead be merely flexible such that upon release of the chest by the CPR provider the frame expands due to the natural resilience of the infant's chest. The frame is illustrated as an open U-shaped frame, but may be most any shape useful to properly locate the sensors above and below the infant's thorax and convenient to dispose about the infant's thorax. So, for example, the frame may be an oval which completely encircles the thorax. The frame may be provided in various sizes, with each size chosen to suit a range of infants and small children of various sizes, or it may be provided in single size suitable for a wide range of patient sizes.

If the system is intended to impart some expansive force on the chest between compression down strokes, during the release phase or upstroke of a compression, the inner surfaces of the extending segments of a resilient frame, which inner surfaces may include the inner surfaces of the sensor assemblies (or housings, if they are discrete from the extending segments), may be covered or coated with an adhesive layer suitable for adhering the extending segments to the thorax of the infants. The adhesive may be limited to the tips of the extending segments, such that only the tips of the extending segments adhere to the chest wall. With this construction, with each release of compression force, the resilient expansion of the frame with exert expansive force on the chest wall, and provide a degree of active decompression between each compression.

Figure 5A:
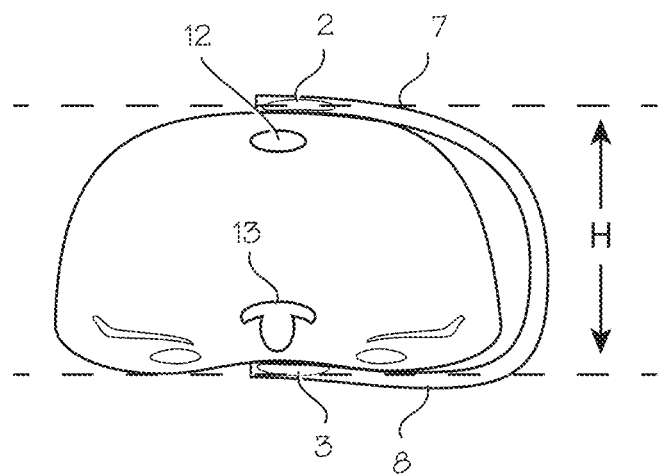
FIGS. 5A, B and C illustrate the compression frame during compressions of the infants thorax.
Figure 5B:
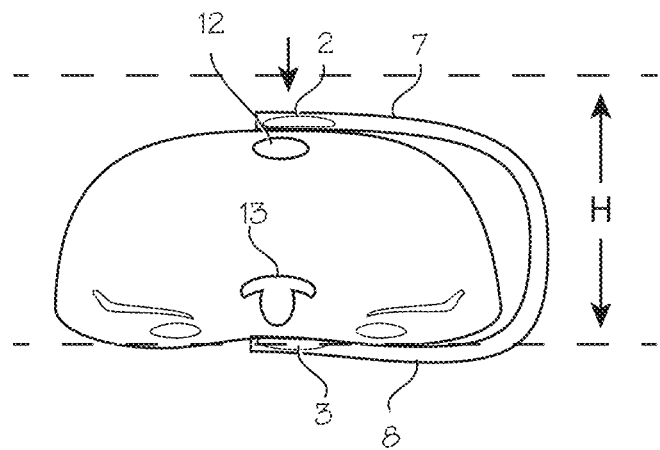
Figure 5C:
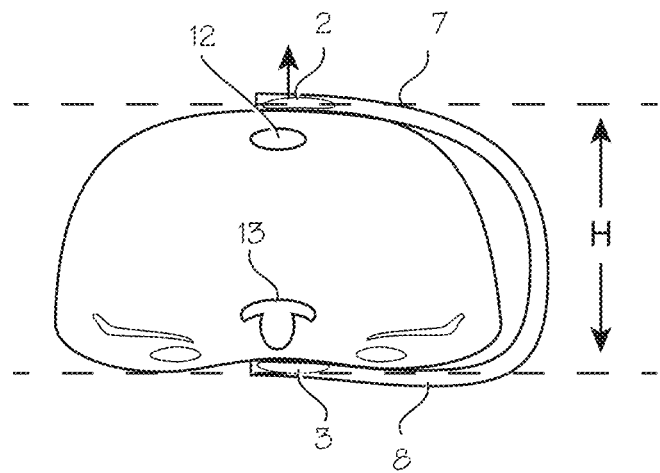

FIGS. 5A, B and C are cross sections of the frame, illustrating the action of the frame on the thorax of the infant. As shown in FIG. 5A, the frame is slipped over the infant's chest, such that the anterior sensor 2 is disposed directly over the sternum 12, and the posterior sensor 3 is located under the spine 13. The CPR provider squeezes the infants chest, using the two-thumbs technique, to achieve the compressed state illustrated in FIG. 5B. FIG. 5B represents the compression stroke or compression phase of the compression cycle. Upon release, the infants chest will expand, as shown in FIG. 5C, to its original thickness. Where the interior surfaces of the extending segments are adhesive, the resilient expansion of the frame lead to an expansive force applied to the chest, which hastens the expansion of the chest during the release phase of the compression cycle.

Figure 6:
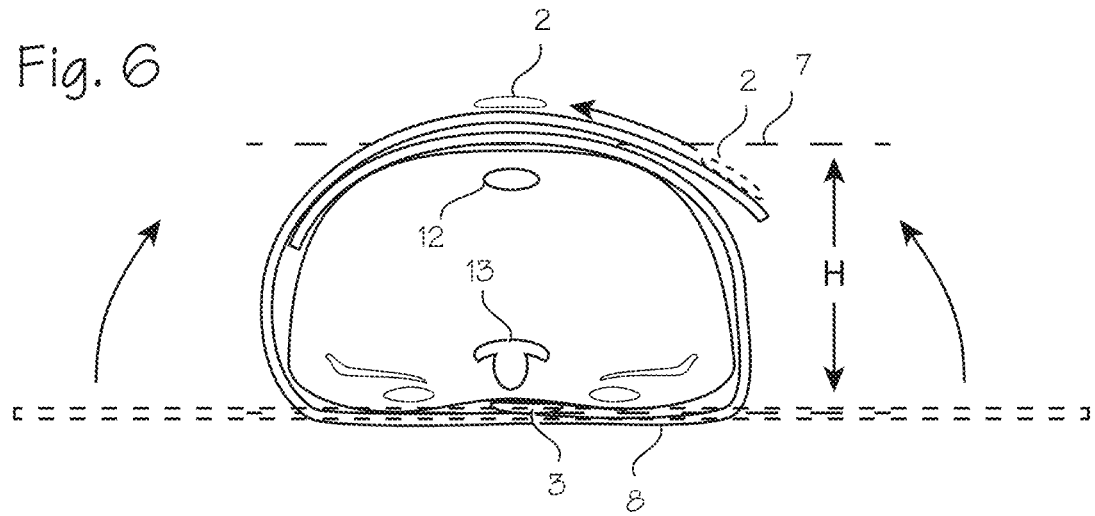
FIG. 6 illustrates a wrap-around frame which can be fitted on an infant cardiac arrest victim.

FIG. 6 illustrates a version of the frame which wraps entirely around the infant cardiac arrest victim. In FIG. 6, the frame 4 may be provided in a length exceeding the circumference of the infant, and sufficient to entirely surround the infant's thorax (practically, the wrap around frame will be provided in a single length long enough to surround infants of various sizes). As with the frames of the earlier figures, the frame of FIG. 6 is resiliently biased to open to a circumference larger than the circumference of the infant. The frame may have an initial configuration which is substantially flat, in which case it is folded up and around the infant's thorax as shown, and adjusted to obtain a close fit with the infant's thorax before compressions are initiated. The frame may instead have an initial configuration which is substantially circular, in which case it is spread open to accommodate the infant's thorax and adjusted to obtain a close fit with the infant's thorax before compressions are initiated. The anterior sensor 2 may be releasably fixed to the frame, with hook and loop fastener or other fastener, so that it can be relocated to the infant's sternum when the frame is adjusted to fit about the infant.

Figure 7:
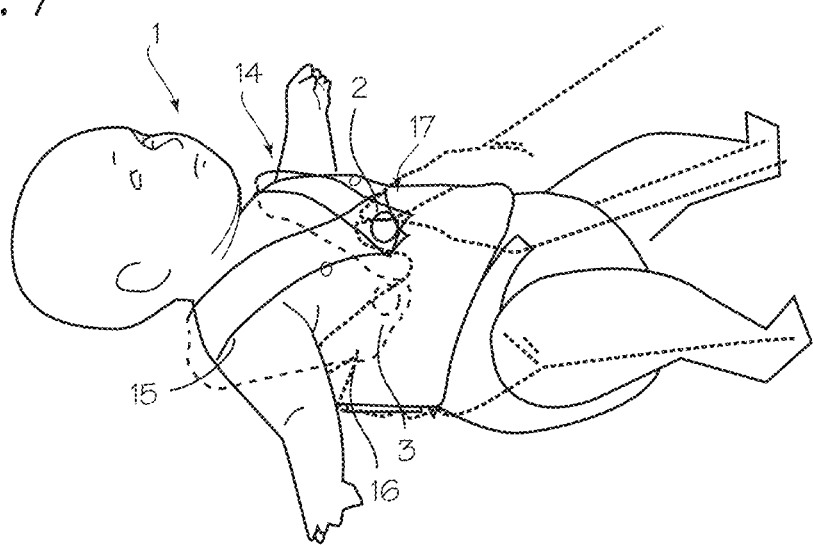
FIG. 7 illustrates a variation of the frame, applied to infant cardiac arrest victim over the shoulders of the infant.

FIG. 7 illustrates a variation of the frame, applied to infant cardiac arrest victim over the shoulders of the infant. The frame of FIGS. 2 through 4 can of course be fitted over one shoulder of the infant, at the option of the CPR provider. The frame 14 of FIG. 7 comprises a front portion 15 and back portion 16, with an opening between the two to accommodate the infant's head. From the side or lateral aspect, the frame is U-shaped. As with the frame of FIGS. 2 through 4, this frame may be resilient and biased to an open position, with the distance between the sensors in the open, relaxed configuration being slightly greater than the anterior-posterior thickness of the infant's thorax. The sensors 2 and 3 are mounted on the frame, with the anterior sensor 2 mounted on the front portion and the posterior sensor 3 mounted on the back portion. As illustrated, viewed from the front or anterior aspect, the front portion is V-shaped, with the vertex 17 of the V, where the anterior sensor 2 is located, disposed over the sternum of the infant. The posterior sensor 3 located directly below the anterior sensor, on the back portion and located at the back of the infant. The vertex of the V serves as an easily recognizable landmark for the user when applying the frame to the infant, but the frame may be made in other configurations that permit the frame to be slipped over the infant's head (for example, a bib or pinafore), and provide for locating the anterior sensor over the infant's sternum.

Figure 8:
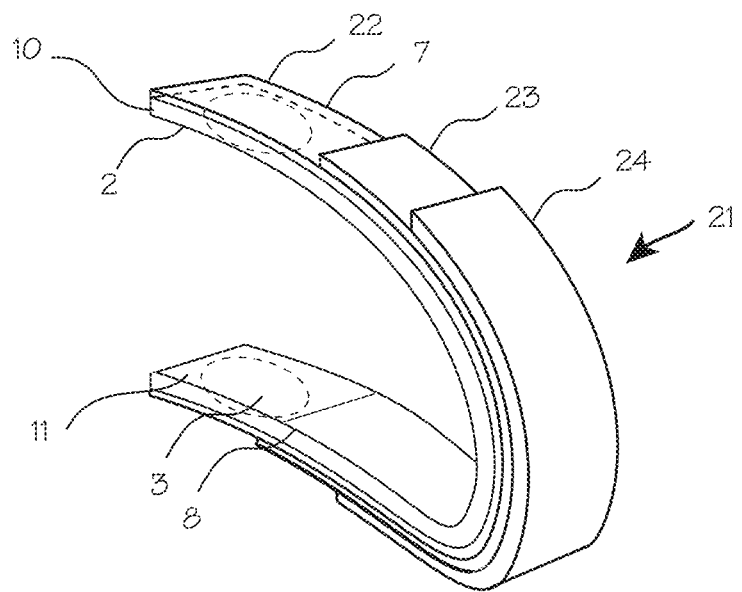
FIG. 8 illustrates a frame for use in the system which can be easily modified to adjust the resilience of the frame.
Figure 9:
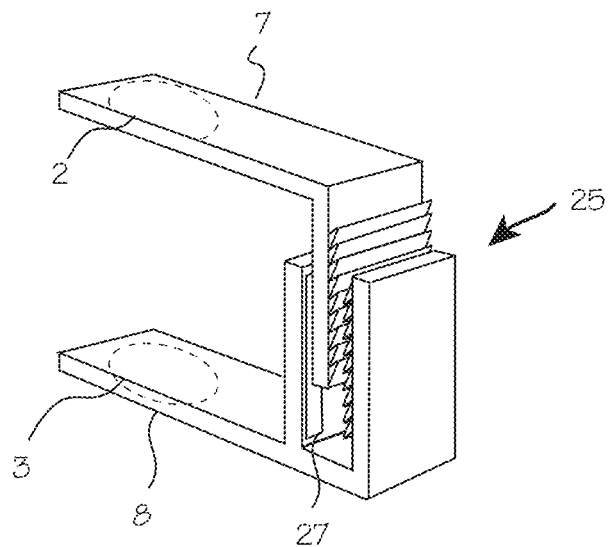
FIG. 9 illustrates a frame for use in the system, which can be adjusted to fit infants of various sizes.

The frame can be provided in a single size chosen to fit most infants subject to the two-thumb technique, and configured with a resilience and expansive force suitable for applying active compression/decompression for most infants, or the frame can provided in a variety of sizes, leaving to a CPR provider to select an appropriate size and/or resilience at the point of use, or adjust size and/or resilience of the frame at the point of use when the size of the actual patient is known. Should it be desirable to adjust these properties, the frame can be modified as illustrated in FIGS. 8 and 9. FIG. 8 illustrates a frame for use in the system which can be easily modified to adjust the resilience of the frame. The frame 21 holds the anterior and posterior sensors 2 and 3 at the tips of anterior and posterior extending elements 7 and 8. The frame 21 is resilient, and manufactured to exert a first level of expansive force when released from compression. The frame comprises one or more additional layers 22, 23 and 24, which are also resilient. The additional layers are secured to the underlying layers with adhesive or a mechanical interlock, such that they are releasable secured to underlying layers and may be removed easily by the CPR provider. To adjust the resilience of the frame, one or more releasable layers may be removed, thus weakening the frame and reducing its resilience.

FIG. 9 illustrates a frame for use in the system, which can be adjusted to fit infants of various sizes. The laterally extending segments 7 and 8 are connected to each other through an expandable ratcheting mechanism 25. The ratcheting assembly may be used to expand or collapse the laterally extending segments 7 and 8 to size the device to a particular infant cardiac arrest victim. As with the U-shaped frames illustrated above, the sensors 2 and 3 are disposed within or on the tips of the extending segments.

The sensors may include any sensor technology suitable for determining compression depth. Accelerometers may be used, as described in Halperin, U.S. Pat. No. 6,390,996 and Palazzolo, U.S. Pat. No. 7,122,014. In this case, the anterior sensor may be an accelerometer-based chest compression monitor as described in Halperin and Palazzolo, and the posterior sensor can be a reference accelerometer or another accelerometer-based chest compression monitor. The accelerometers are capable of producing acceleration signals corresponding to the acceleration of the chest and the acceleration of the back, and the control system is operable to integrate the acceleration signal received from the accelerometers, integrating and combining those signals to determine the depth of chest compression and produce a measured depth signal. The control system is also programmed to report the measured depth to the CPR provider through the display or audio output, or compare the measured depth signal to a desire depth of compression and report to the CPR provider whether the achieved depth of compression meets or fails to meet the desired depth. Velocity sensors may also be used, in which case the control system is programmed to process the velocity signal received from the velocity signals to achieve the same ends. Also, the control system may be programmed to process the acceleration signals to determine the compression velocity, release velocity, and compression rate to produce corresponding signals, and provide reports and feedback to the CPR provider regarding these parameters.

Magnetic motion sensors, such as those which use an electromagnetic source and sensor, described in Geheb, et al., Method and Apparatus for Enhancement of Compressions During CPR, U.S. Pat. No. 7,220,235 (May 22, 2007) and Centen, et al., Reference Sensor For CPR Feedback Device, U.S. Pub. 2012/0083720 (Apr. 5, 2012), may also be used to determine compression depth. In this case, the one sensor is a magnetic field sensor, and the other sensor is replaced by a magnetic field generator (a permanent magnet or an electromagnet), and the control system is operable to receive and process distance information from the electromagnetic sensor to determine compression depth, release velocity, and compression rate. These and any other means for determining compression depth, compression rate, and release velocity may be used.

The control system is programmed to receive signals corresponding to motion of the chest wall and motion of the thorax (motion of the back, as sensed by the sensor 3), and determine the depth of compression achieved during CPR based on those signals. (In the magnetic sensing embodiment, the control system is programmed to determine the depth of compression achieved during CPR based signals from the magnetic field sensor.) The control system is programmed to generate a signal corresponding to the determined chest compression depth which may be used to provide a display indicating achieved chest compression, or may be used by other equipment. The control system is further programmed to compare the determined depth of compression with predetermined desired chest compression goals, and provide feedback to a CPR provider regarding the adequacy of chest compression depth, including whether achieved chest compression depth is inadequate, adequate, or excessive as compared to the predetermined goals. The feedback can include audio or visual prompts to compress more deeply, prompts to compress at a faster or slower rate, and prompts to quickly and completely release the chest of the patient after each compression. The feedback can also include haptic feedback, provided when compression depth is adequate, inadequate, or excessive, through vibrators disposed on the frame.

The system can be adapted to determine an initial measurement of the patient's chest. The sensors mentioned above may be used, or additional sensors may be added to the frame, to measure the patient's chest prior to the start of chest compressions. This information can be used to advise a CPR provider to limit expansive motion of the frame during release (to limit the active decompression)(limiting the expansive motion of the frame during release can be accomplished merely by holding the frame between compressions, and not allowing it to fully expand), and to advise the CPR provider regarding the adequacy of chest compressions based on the size of the patient. The distance between the sensors 2 and 3 can be determined, using signals from the sensors, where applicable. For example, where the sensors are a magnetic field sensor and a magnetic field generator, the position of the magnetic sensor in the magnetic field generated by the magnetic field generator can be determined.

Additional sensors may be used to size the patient. Distance sensors and proximity sensors at the tips of the frame, near sensor 2, for example, can determine the distance from the frame tip to the patient, and thereby calculate the size of the patient. This system may require operator input, to inform the system when the frame is disposed about the patient such that the bottom frame tip and sensor 3 are in place below the patient, so that the control system can then calculate the patient chest height based on the known distance between the frame tips and the measured distance between the upper frame tip and the chest wall of the patient. In another system, strain sensors disposed on or within the frame can be used to determine the shape of the frame, and thus the distance between the frame tips. For example, a shape monitoring cable (comprising linear arrays of fiber Bragg gratings may be disposed on or within the frame, and a control system may operate a light source and light sensors to determine the shape of the frame. This system may require operator input, to inform the system when the frame is disposed about the patient such that the bottom frame tips and sensor 2 and sensor 3 are in contact with the patient, so that the control system can then calculate the patient chest height based shape of the frame as determined by the shape monitoring cable. Shape monitoring cables suitable for use in this embodiment may also include piezo-electric strain gauges and other forms of strain gauges.

For the frame of FIG. 9, an optical, magnetic or capacitive encoder or other position sensor 27 can be used to determine the position of ratcheting segments relative to each other, and from this information the control system can determine the distance between the tips and the chest height of the patient. Again, with operator input informing the system when the frame is disposed about the patient such that the bottom frame tips and sensor 2 and sensor 3 are in contact with the patient, the control system can then calculate the patient chest height based on the encoder reading. Thus, for the initial determination of the size of the patient, sensors mounted on the frame tips, encoders disposed on an adjustable portion of the frame, a shape monitoring cable disposed on the frame, and any other suitable means of determining the distance between the frame tips can be used, in conjunction with input from the CPR provider indicating that the frame tips are in close proximity to the patient/s thorax.

In each case, the initial measurement of the size of the patient's thorax can be use by the control system to select advisory parameters, such as the amount of compression desired, and the amount of active decompression desired, for the patient based on patient size, and generate advisory prompts to the CPR provider based on patient size. The compression depth targets for infants should be about ⅓ of the infant's chest height, and the appropriate chest compression goals can be selected by the control system programmed to calculate the chest compression goals based on the measured size of the patient. Thus, for CPR compressions performed on small children, the control system would be programmed to provide a positive advisory (that compression are adequate) or a negative advisory (that compression are excessive, or active decompression too expansive) for small compressions and active decompressions, and also programmed to provide a positive advisory (that compression are adequate) or a negative advisory (that compression are excessive, or active decompression too expansive) for slightly larger compressions and active decompressions for CPR performed on a larger child.

In use, a CPR provider will place the frame around the thorax of an infant cardiac arrest victim, with one sensor on the victim's chest, over the victim's sternum, and the second sensor under the infant's spine. The CPR provider will then grasp the infant's thorax with both hands, placing his thumbs over the infant's sternum and extending his fingers around the thorax, in the two-thumbs position. The CPR provider will perform CPR compressions, using the two-thumbs technique, pressing down on the chest, keeping the anterior sensor between his thumbs and the victim's chest, so that the sensor moves up and down in fixed relation with the patient's chest, and keeping the posterior sensor between his fingers and the victim's spine, or at least keeping the posterior extending element between his fingers and the patient's back so that the posterior sensor moves up and down in fixed relation with the patient's back. The CPR provider will operate an associated control system, and energize the sensors, to analyze the sensor signals to determine chest compression depth, velocity of the compression monitor (including release velocity), and the rate of compression, compare the determined chest compression depth, release velocity and/or compression rate to the desired values, and operate an output device to provide prompts indicating whether the determined chest compression depth, release velocity and/or compression rate meets or fails to meet the desired values. The control system may also be operated to compare the measured depth of compression to a desired depth of compression and report to the CPR provider whether the achieved depth of compression meets or fails to meet the desired depth. Prior to the start of compressions, the CPR provider may optionally bring the anterior frame and posterior frame into contact with the body, and provide input to the control system that the anterior frame and posterior frame are in contact with the body.

The frame may be used to perform CPR compressions, including active compression/decompression, with or without the compression depth monitoring components of the system. The frame, with an adhesive surface on at least a portion of the interior surface of the anterior segment, can be installed about the thorax of a patient such that the adhesive secures the anterior segment to the patient's chest wall, over the sternum (that is, the preferred compression point). With the frame installed, CPR compressions are performed. Upon release of each compression, the resilient frame will resiliently expand toward its open configuration, thereby imparting some expansive force on the chest wall. If the patient is prone on a supportive surface, only the anterior segment need be adhesive. If the patient is held up, or prone on a soft surface, the posterior segment interior surface may be adhesive as well. This method may be used on adults and pediatrics as well as infants.

When used to provide CPR compressions with active compression/decompression the method entails providing the frame having an anterior segment and a posterior segment, and sized and dimensioned to fit at least partially around the thorax of the cardiac arrest victim with adhesive on a portion of the anterior segment is adhesive and, optionally, on the posterior segment, and installing the frame about the thorax of a cardiac arrest victim such that the adhesive secures the anterior segment to the cardiac arrest victim's chest wall. After installation, the CPR provider performs CPR chest compressions on the cardiac arrest victim, allowing the frame to expand between compressions to provide active decompression, with the resilience of the frame acting to restore the frame toward its relaxed opened position and thus exert upward pulling force on the thorax.

The augmented release devices described in relation to the following figures provide for CPR with active decompression during the release phase following each compression, and can be used with manual or automated chest compression (e.g. as provided by a belt-driven chest compression device or a piston-based chest compression device). The augmented release devices may comprise one or more resilient portions and be shaped to conform to the chest of a human patient. The inner surface of the augmented release device facing the body of a patient is capable of adhering to the skin of the chest of the patient, for example, part or all of the inner surface may be coated with adhesive on the body facing side and secured to the chest of the patient immediately before or during chest compressions. The augmented release device is capable of transitioning between a compressed and uncompressed state. During each chest compression, the device is compressed, along with the chest of the patient, under the compression forces applied by the CPR provider or the automatic chest compression device. During each release phase of the compression cycle, the device may open in a manner according to natural chest expansion. For example, the augmented release device may comprise one or more arcuate bands comprising resilient portions. The arcuate bands may open upward in an anterior direction (along the anterior-posterior axis of the chest), in a lateral direction (along the lateral or transverse axis to expand the chest), in a superior direction (along the superior-inferior axis of the chest), in a pump-handle motion, bucket-handle motion, or any combination of these motions, thus exerting de-compressive force on the patient's chest. The arcuate bands may be provided in the form of left and right spring elements, with arcuate C-shapes or U-shapes, and may resemble the shape of natural ribs and closely match the contours of the patient's thorax, or they may take the form of rectilinear C-shapes or U-shapes (as in FIG. 9). The arcuate bands may be sufficiently conformable to the thorax such that the portion of the spring elements secured to the thorax will follow the movement of the thorax during compressions, while also being sufficiently resilient that they rebound to their uncompressed configuration when not compressed, and are configured to be affixed to a thorax of a cardiac arrest victim. The articulating flexible joint may be a resilient junction between the arcuate band and the spine 36, formed integrally of a single piece, or it may be a hinged joint between the spine and the posterior terminus of the arcuate band. The one or more arcuate bands may be biased to an open configuration for use with manual or automated CPR, or be actively rotated using the motors, belts or pistons of the CPR chest compression device.

Figure 10A:
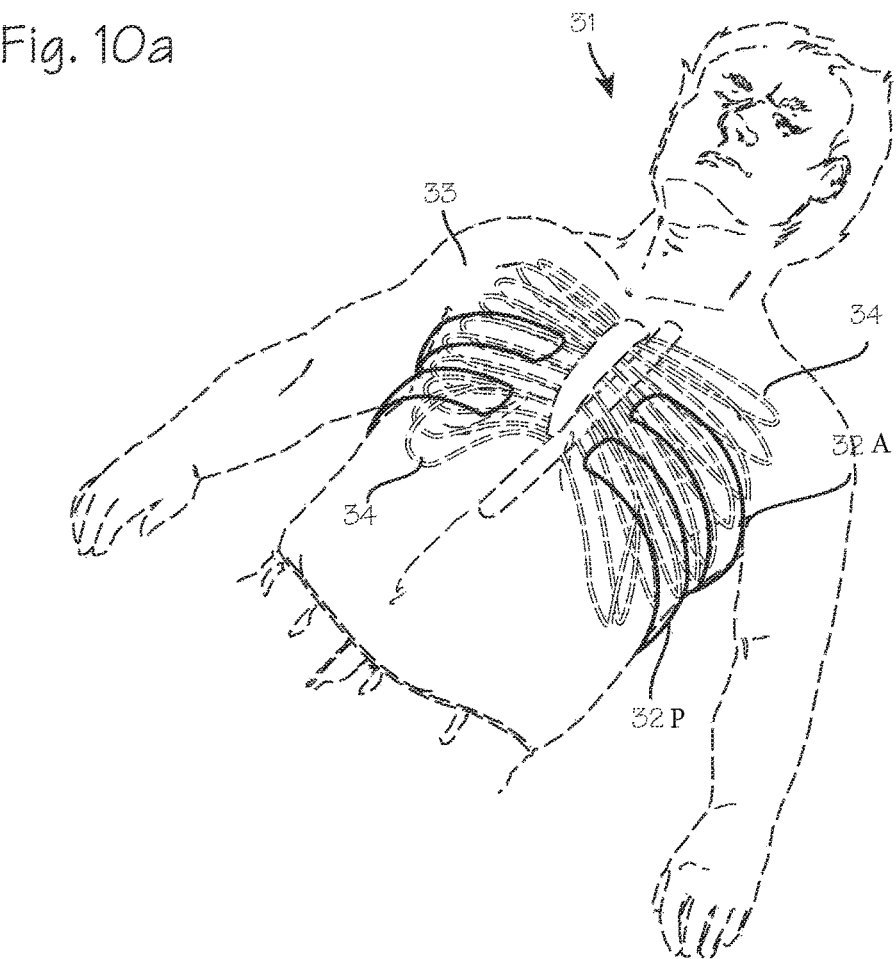
FIG. 10a shows a perspective view of a patient fitted with an augmented release device with one or more arcuate bands joined to a spine secured over the chest of the patient.

FIG. 10a shows a perspective view of an adult cardiac arrest patient 31 fitted with an augmented release device. The augmented release device includes resilient portions 32 secured over the chest 33 of the patient. FIG. 10a shows the patient's ribs 34 in phantom, with approximately C-shaped bands encircling and conforming to the patient's chest. The bands conforming to the chest are resilient, such that they are capable of being compressed and subsequently transition back to their original uncompressed shape upon release. The bands may be constructed to be resilient, for example, by constructing them from a material that has the ability to change shape elastically and release back to its original state, by including spring-like elements as part of the arcuate band, by constructing the arcuate band with both rigid and resilient portions, etc. Resilient materials for use in constructing the device include metals (such as stainless steel, nitinol, spring steel, beryllium copper, etc.) or plastics and/or polymers (such as polyurethane, polyethylene, polycarbonate, fiber reinforced plastic, etc.). The resilience may alternatively be a result of including a mechanical element (such as gears, rotors, etc.) to bias the arcuate band to an open configuration. When provided in a form which may be driven by motors, the arcuate portions can be made of resilient materials or more rigid materials.

Figure 10B:
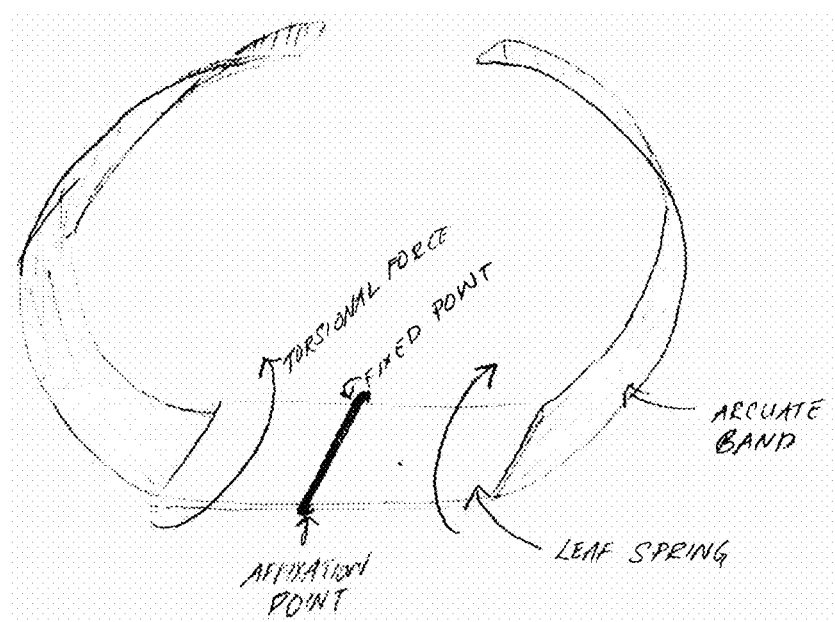

The resilient property may be achieved by including spring or spring-like components as part of the augmented release device, for example, a spring-like component can be included at the posterior end of the device (which is placed under the patient's back) and joined to one or more arcuate bands at the posterior ends of the bands. FIG. 10b describes such an augmented release device constructed by joining a spring-like component to two arcuate bands. In this example, the spring-like component is a flat spring which is made of resilient materials and the arcuate band may be rigid or have some elasticity. The flat spring may be made of a flat strip material and or constructed into an approximately flat strip using resilient materials, e.g. high carbon spring steel, nickel-silver, high-nickel alloys, stainless steel, phosphor bronze, plastics, polymers, etc., such that when deflected by an external load, it stores and releases energy. The flatness of the spring may be defined by an aspect ratio such that the ratio of maximum length to maximum thickness is more than 4 to 1. In other examples the spring-like component may be a coil, a rod or oval shaped portion made of resilient material, etc. Where the device comprises two arcuate bands encircling either side of a patient's chest, the spring-like component will have a central affixation point. The affixation point may be held in place by the weight of the patient, such that the parts of the spring-like component on either side of the affixation point are capable of torsional movement. During chest compressions the spring-like component, e.g. flat spring, will experience torsional movement. During chest release, the spring-like component will return to its original state and may be capable of exerting a torque of about 1 to 10 foot pounds about the lateral axis, as described in FIG. 10b.

The resilient portions of the augmented release devices provide expansive forces spread widely over the patient's chest, for a total of 1 to 25 pounds of force, and preferably about 10 pounds of force. The resilient portions may be constructed of one or more arcuate bands 2 to 6 inches wide, to provide a wide area for adhering to the skin of the thorax, and 12 to 36 inches long to partially encircle a wide range of patients, including in some examples with overlap in the areas of the sternum depending upon the size of the patient.

The augmented release device may alternatively include two or more resilient portions joined to a central portion. For example, as shown in FIG. 11, the augmented release device 35, may include two or more arcuate bands 32 joined to a spine 36 through an articulating flexible joint 37. Each arcuate band comprises a laterally extending anterior segment 32A and a laterally extending posterior segment 32P. FIG. 11 shows the relationship between the arcuate bands and the spine. The arcuate bands 32 extend laterally from the spine 36, and curve first upwardly and then medially such that the anterior (or head) ends terminate above the spine 36. The arcuate bands may also slant inferiorly along the superior-inferior axis 38 of the assembly. FIG. 12 shows the augmented release device of FIG. 11 in a compressed, small diameter configuration. This configuration is achieved upon compression of the patient's chest, when the device is disposed about the patient and adhered to the chest of the patient. As illustrated in this Figure, upon expansion, the arcuate portions may rotate in an abducting manner, rotating about the joint between the arcuate portion and the spine, and may also rotate in a pump handle motion, about a lateral axis 39 passing laterally near or through the spine, or a combination of both motions. As illustrated in FIG. 11, the posterior or head end is secured to the spine, and the arcuate band is sized and dimensioned such that, when disposed about a cardiac arrest victim with the spine under the cardiac arrest victim, the anterior or sternal end is disposed over an anterior portion of the cardiac arrest victim.

In some versions, there may be an articulating flexible joint that may have a resilient junction between an arcuate band 32 and a central portion (e.g. the spine 36) formed integrally of a single piece, or it may be a hinged joint between the central portion and the posterior terminus of arcuate band. In another example, the device may be made with corresponding left and right arcuate portions formed integrally in a single, approximately C-shaped band, which partially encircles and conforms to the chest, dispensing with a discrete central structure. For example, the device may be a single resilient arcuate band of about 3 to 6 inches width and about 12 to 36 inches long. For example, the resilient band may be about 3 inches wide and about 15 inches in length.

The augmented release devices may be sized and dimensioned to fit partially, or completely, around the chest of a typical patient (a single size may be provided for a wide range of potential patients, or the device can be provided in multiple sizes leaving it to paramedics to select an appropriate size for each patient). The augmented release device may also include one or more straps that encircles the patient's shoulders to hold one or more arcuate bands in place during CPR. The straps may be attached to the anterior ends of the arcuate bands or to a part lateral to the anterior ends. The straps may provide tension on the attached point to aid movement of the arcuate bands, for example, in the superior direction.

The augmented release devices are capable of being adhered to the chest of a patient, as depicted in FIGS. 20*a* and 20*b*. The inner surface of the anterior end of the one or more arcuate bands may have an adhering surface 60 that binds the end of the arcuate bands to the surface of the patient's chest, as shown in FIG. 20*a*. The anterior of the arcuate bands may be adhered to the skin above the patient's sternum, or may be adhered to the skin above a part of the patient's chest lateral to the sternum. In additional examples, the entire inner surface of the augmented release device may be adhered to the skin of the patient's chest. The adhering surface 60 may be composed of an adhesive gel such as is used for solid-gel defibrillation electrodes such as ZOLL Stat-Padz (Chelmsford Mass.). Alternatively, a double-backed polyethylene foam tape, such as 3M tape 4496 (3M, Minnesota) may be used to bond the anterior end of the arcuate bands to the anterior surface of the patient's thorax. The arcuate bands may also be adhered with flexible and/or elastic webbing and a releasable closure (VELCRO® hook and loop fastener, snaps, etc.). Referring to FIG. 20*b*, in another embodiment, the adhering surface 60 may be composed of a compliant molded element with multiple suction cups 62 disposed on the surface facing the patient. When pushed onto the patient, the multiple suction cups 62 will each bind to the surface of the chest.

The one or more arcuate bands 32 may extend so that the anterior ends of the arcuate bands are positioned lateral to the patient's sternum and sternal cartilage, as shown in FIG. 10*a*. The adhering surfaces 60 may be attached to the chest just superior to the inferior costal margin, lateral to the sternal notch. In this example the rescuer's hands do not press directly against the augmented release device during chest compressions, nor do the arcuate bands of the device pull up directly from the sternum or manubrium. Alternatively, the one or more arcuate bands of the device may extend to cover the patient's sternum and thus the rescuer will be pushing down onto the anterior (or sternal) ends of the arcuate bands during chest compressions. The resilient portions may be constructed as shown in FIG. 12 such that lateral portions work in conjunction with vertical portions to cause the hinging of the patient's sternum and ribs during active decompression to more closely resemble the natural pump-handle and bucket-handle actions of the rib cage and thorax. By specifically pulling upward and superiorly in a motion that is closer to the natural pump-handle motion, sternal, manubrial and costal injuries are likely to be reduced.

The augmented release devices may be employed to cause the pump handle or bucket-handle motions, or both types of motion simultaneously. For example, referring to FIG. 21, one or more arcuate bands of the device are constructed so as to create a force-vector 65 on the chest that aids the pump-handle active decompression phase and improve circulation to the cardiac arrest victim during chest compressions. For example, where the anterior ends of the one or more arcuate bands are adhered to the patient's skin above the sternum, during release the force applied by the anterior end of the one or more arcuate bands on the patient's sternum may not be purely upward in direction, such that the force-vector deviates from the anterior-posterior axis. The force vector may deviate from the anterior-posterior axis by at least about 5 degrees or more, up to about 60 degrees, in the superior direction (along the superior-inferior axis, thus aiding the natural pump-handle motion of the chest). The force-vector may also have a lateral component, deviating from the anterior-posterior axis by at least about 5 degrees, up to about 60 degrees, in the lateral direction. The force exerted by the one or more arcuate bands on the adhered part of the patient's skin may be in the range of 1 to 10 pounds during a release phase of a chest compression cycle.

The one or more arcuate bands of the augmented release device may instead be adhered to the patient's chest lateral to the sternum and, as described above, the adhered portion may exert a force on the chest that is not purely upward, but deviates from the anterior-posterior axis in the lateral and superior directions. The force vector may deviate from the anterior-posterior axis by at least about 5 degrees or more, up to 90 degrees, in the lateral direction (along the lateral or transverse axis, thus expanding the chest). The force vector may have a superior component, deviating from the anterior-posterior axis by at least about 5 degrees or more, up to about 60 degrees, in the superior direction.

The manner of adhering the device to the patient can be employed to selectively apply pressure at particular points or over the entire inner surface in contact with the patient's chest. The augmented release device may have one or more arcuate bands, or one resilient arcuate band, that wrap entirely or partially around the patient's chest and the points of adherence with the skin of the patient may be distributed over the inner surface to modify the strength and direction of the force on particular parts of the chest during compression and release. Also, the number of adhering contacts that are applied to a patient can be varied depending upon the size of the patient, such that more contacts may be used for a larger patient to increase the forces applied in both the anterior and lateral directions.

As one example of selectively applying pressure at particular points, the augmented release device may be constructed as described in FIGS. 22a and 22b. The device may be constructed with one or more arcuate bands, e.g. one resilient arcuate band or two arcuate bands joined to a spring-like component, that can be wrapped around the patient and have a lateral diameter that is biased into an open configuration with a diameter larger than that expected for the largest typical patient in either a compressed or uncompressed state. The one or more arcuate bands may be configured to adhere to the patient's chest at both anterior ends of the arcuate bands (above or near the sternum) as well as on the lateral most sides of the patient's chest (to the left and right sides of the patient's chest). During chest compression (e.g. by a CPR provider) the anterior ends of the arcuate bands will move downward and during release the anterior ends will move upward. With respect to the force on the sides, during compression the patient's chest will expand laterally (as the ribs flatten) under the pressure of the compression and, as a result, the outward biased force caused by the arcuate band or bands on the adhered lateral side of the patient will decrease relative to the outward force on the adhered chest when uncompressed, as described in. Upon decompression (when the rescuer or mechanical chest compression device releases the chest), the outward bias force exerted by the arcuate band or bands on the sides of the chest will increase (as the ribs restore to their uncompressed state), exerting a counter pressure on the adhered part of the arcuate band, which is biased to remain in a diameter larger than the patient's chest. In this manner the expansion of the chest will be aided in the bucket-handle movement, to improve circulation to the patient's chest. The outward force upon decompression may be between 1 and 25 lbs, and preferably between about 5 and 10 lbs. The large diameter bias of the arcuate band can be achieved by constructing the arcuate part with a material capable of maintaining its shape, yet exhibiting sufficient elasticity to conform to the chest of the patient. Alternatively, in a device such as that described by FIG. 10b, the spring component can be curved, with the concave portion facing the back of the patient's body, such that the spring flattens (and extends) when downward force is applied by the CPR rescuer. Upon the spring extending, the arcuate bands are extended outward, applying lateral pressure on the sides of the patient's chest.

Where the entire inner surface of one or more arcuate bands is adhered to the skin of the patient's chest, the lateral sides of the arcuate bands may exert a force in the lateral direction, and the anterior portions may exert a force in the upward as well as the superior directions. In such a device the arcuate bands may be constructed from an elastic material and be shaped to conform to the patient's chest. The one or more arcuate bands may expand along with the chest to exert an outward pressure over the entire surface in contact with the patient's skin, adapting to the natural movement of the chest during chest release.

FIG. 13 shows a cross section of an example of the augmented release device 35 fitted about a patient 31. In relation to the patient, when the device is fitted on a patient, central portion 36 is disposed under the spine 13 of the patient, and the arcuate bands 32 extend laterally from the central portion 36, along the back of the patient, and then curve first upwardly following the lateral surface of the patient's chest (following the patient's rib cage) and then medially to terminate above, or lateral to, the patient's sternum 12. The anterior terminus or tip 40 of each arcuate bands may fall just laterally of the sternum, although exact lateral spacing between the terminus and the patient's sternum will vary depending on the relative size of the patient and the assembly. All or part of the inner surface 41 of the augmented release device is adhered to the skin of the patient's chest. With the patient thus fitted with the augmented release device, a CPR provider can compress the chest of the patient, with hands 42 compressing on the sternum for the compression stroke. As shown in FIG. 14, the compression stroke compresses the chest and forces the sternum of the patient toward the spine. As shown in FIG. 15, release of the compression, when the CPR provider removes his/her weight from the patient to provide the release phase of the compression cycle, results in resilient expansion of the chest and resilient expansion of the arcuate bands upwards, as well as in the lateral and superior directions, aiding in the natural pump-handle expansion of the chest.

The augmented release devices may be used for both manually delivered compressions and with mechanical compression units (e.g., LUCAS® or AUTOPULSE® mechanical chest compressors). As shown in FIG. 16, the augmented release device can be used in conjunction with a compression monitor 2, which may be connected to the anterior tips 40 of either end (32L, 32R) of the resilient portion or portions.

As shown in FIG. 17, the augmented release device may be combined with an automated CPR chest compression device. FIG. 17 illustrates the chest compression device, similar to the AUTOPULSE® CPR chest compression device, fitted on a patient 31. A chest compression device 44 applies compressions with the belt, which has a right belt portion 45R and a left belt portion 45L, including load distributing panels 46R and 46L designed for placement over the anterior surface of the patient's chest while in use, and tensioning portions which extend from the load distributing portions to a drive spool, shown in the illustration as narrow pull straps 47R and 47L. (The entirety of the compression belt is referred to as a "load distributing band" in the art.) The right belt portion and left belt portion are secured to each other with hook and loop fasteners. A bladder 48 is disposed between the belt and the chest of the patient. The narrow pull straps 47R and 47L of the belt are spooled onto a drive spool located within the platform to tighten the belt during use, passing first over laterally located spindles 49L and 49R. The chest compression device 44 includes a platform 50 upon which the patient rests which also provides a housing 51 to house the various components. Means for tightening the belt, a processor and a user interface are disposed within the housing. In the commercial embodiment of the device, the means for tightening the belt includes a motor, a drive train (clutch, brake and/or gear box) and a drive spool upon which the belt spools during use.

The drive spool 52 and the spline 53 which fixes the belt to the drive spool are located within the housing 51, as is a motor and computer control system which operate to drive the drive spool to spool the belt, thereby tightening the belt about the chest and thorax of the patient and a resuscitative rate to accomplish CPR. The anatomical landmarks shown in this Figure include the sternum 12, the spine 13, and the right and left scapula 54R and 54L of the patient. Referring to the landmarks, the chest compression band is wrapped around the patient such that the load distributing portions are located on the chest (that is, the anterior surface or portion of the thorax), over the sternum, with the narrow strap portions descending from the load distributing portions to wrap around the lateral spindles and thence run to the drive spool. The lateral spindles are spaced laterally from the medial centerline of the device so that they are disposed under, or lateral to, the scapulae of the typical patient, so that tightening of the compression band results in anterior/posterior compression of the chest.

To provide active decompression in this system, the augmented release device 35 is disposed between the compression belt and housing. The device may be constructed to have one or more arcuate bands 32 and a central portion 36, as illustrated in FIGS. 11 through 15, or arcuate bands may arise directly from the backboard, as shown in FIG. 18. In operation, the compression device operates by spooling the straps about the drive spool, which tightens the entire belt to compress the thorax of the patient. As the belt tightens to compress the thorax (and the patient's rib cage), it also compresses the arcuate bands, folding them to a small diameter configuration. When the chest compression device operates to loosen the belt, the thorax relaxes and expands due to its own resiliency, aided and speeded by the resilient expansive motion of the arcuate bands. The arcuate bands add some load on the compression stroke and thus lead to faster battery depletion, but battery run time is currently more than sufficient for all but the most extended resuscitation attempts.

In self-expanding embodiments described above, the augmented release device is biased in an open configuration which corresponds to the configuration of the portions when uncompressed. The open configuration has a predetermined diameter or circumference which may be slightly larger than an expected diameter or circumference of the largest typical patient to be treated. At the same time, the one or more arcuate bands are compressible to follow the compression of the largest typical patient and a smallest typical patient. For example, the current commercial embodiment of the AUTOPULSE® chest compression device is designed for use with patients with a chest circumference ranging from 29.9 inches (76 cm) to 51.2 inches (130 cm). This provides a device that works well for a wide range of patient sizes, though such devices could be provided in many sizes, leaving it to CPR providers to select a chest compression device of a size to match individual cardiac arrest victims. Likewise, the augmented release device can be provided in a configuration with an unconstrained maximum expanded to a circumference of about 51.2 inches (130 cm) or more. An augmented release device of a single one-size-fits-most may provide different levels of de-compressive and expansive force for patients of different size, the force needed to provide active decompression can vary over a wide range while still providing the benefit of active decompression.

FIG. 19 illustrates an augmented release device in combination with an automated chest compression device in which the one or more arcuate bands are driven by a motor (which may be the same motor used to drive the compression belt). The CPR chest compression 44 device is similar to the device of FIG. 17, with the compression belt (right belt portion 45R and a left belt portion 45L), load distributing panels 46R and 46L, pull straps 47R and 47L, and the bladder 48. The arcuate bands are disposed between the belt and the thorax of the patient. The arcuate bands are attached through gears 55 or a gear assembly, or other linkages to the motor drive shaft or drive spool, to force the portions to close to the small configuration during the compression stroke and open to the large configuration during the release phase. The arcuate bands in this configuration are preferably rigid, but may also be resiliently biased to the open configuration. In the embodiment, the arcuate bands are actively expanded during the release stroke through the action of the motor. Other means for actively driving the arcuate bands toward the open configuration may be employed. These may include use electro-restrictive polymers, shape memory polymers, and shape memory metals, in combination with a power supply and control system operable to apply power to the electro-restrictive polymer or shape memory resilient portions during the release phase.

The mode of adhering the augmented release device to the skin of the patient may be, as previously described, any suitable adhesive, and need not be a strong adhesive, especially in the embodiment used in conjunction with a compression belt, which will force the augmented release device into contact with the skin of the thorax during each compression. The augmented release device may also be fixed to the thorax with one or more suction cups or secured to the patient natural ribs, or the patient's sternum, with osseous screws.

In use, a CPR provider treating a cardiac arrest victim will place the augmented release device about the thorax of the cardiac arrest victim, with the spine of the device under the spine of the patient, and the anterior/sternal ends of the arcuate bands disposed over the anterior surface of the thorax. The CRP provider will then affix the device to the patient, by pressing the arcuate bands into contact with the skin of the thorax to ensure that the adhesive surfaces adhere to the thorax (or otherwise appropriately operate alternative affixation mechanisms). With the augmented release device secured to the patient, the CPR provider with then provide CPR compressions to the patient. For manual compressions, the CPR provider will compress the chest with both hand pressing down on the patient's sternum, with any portion of the arcuate bands that extend over the sternum trapped between the CPR provider's hands and the patient's sternum. For automated CPR with a chest compression device, the CPR provide will install the chest compression device over the arcuate bands. In the case of a chest compression device which uses a compression belt, the CPR provider will apply the compression belt over the arcuate bands. In the case of a piston-based CPR compression device, such as the LUCAS® device disclosed in Steen, the CPR provider will place the LUCAS® device, including the legs and compression unit, around the thorax of the patient, with the arcuate bands disposed between the legs of the device and the thorax of the patient.

In operation, the action of the augmented release device during the release phase of the chest compression cycle, whether by resilient return to an open, large diameter configuration or driven by a motor to an open, large diameter configuration, includes rotating arcuate portions about an inferior/superior axis relative to the patient or, coincidentally, the central portion, or a transverse axis passing through or close to the central portion, or a combination of both rotations, will mimic the natural expansion of the patient's rib cage, but add a component of force to aid in the natural expansion of the chest, such as by a pump-handle motion.

Conversely, during the compression phase, whether driven by downward force of manual compression or piston-based compression to the smaller diameter configuration or driven by a motor to the smaller diameter configuration, motion of the resilient portions includes rotating arcuate portions about a superior-inferior axis relative to the patient or, coincidentally, a central portion, or a transverse axis passing through or close to the central portion, or a combination of both rotations, and will mimic the natural compression of the patient's rib cage.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A device for augmenting chest release of the chest of a cardiac arrest patient during CPR comprising:
    one or more arcuate bands configured to conform to the chest of the patient,
    at least a part of an inner surface of the one or more arcuate bands configured to be adhered to the chest of the patient,
    wherein, for a chest compression cycle having one compression phase and one release phase, the one or more arcuate bands have the capacity to transition between a compressed state during administration of the compression phase of the chest compression cycle and an uncompressed state during the release phase of the chest compression cycle,
    wherein the device is configured to augment the release of the chest of the cardiac arrest patient during CPR by exerting an expansive force on the thorax of the patient to hasten expansion of the chest during the release of the chest relative to unaided expansion of the chest, wherein the expansive force is exerted by decompression of the one or more arcuate bands upon the release of the chest during the release phase of the chest compression cycle; and
    wherein the one or more arcuate bands comprise a first tip and a second tip, wherein the one or more arcuate bands are configured to extend continuously around the patient's back, and wherein the first tip and the second tip are configured to be spaced from each other over a portion of the thorax of the patient.

2. The device according to claim 1, in which the one or more arcuate bands are biased to an open configuration in the uncompressed state.

3. The device according to claim 2, comprising two arcuate bands of the one or more arcuate bands joined by a spring, wherein the device has a lateral diameter larger than the chest of the patient in the uncompressed state.

4. The device according to claim 3, wherein the one or more arcuate bands are configured to be attached to the chest of the patient at anterior ends above or near the sternum.

5. The device according to claim 2, wherein the one or more arcuate bands consist of one resilient arcuate band configured to substantially encircle the chest of the patient.

6. The device according to claim 1, in which the one or more arcuate bands are configured to transition to the uncompressed state during the release of the chest.

7. The device according to claim 1, in which the one or more arcuate bands are configured to be adhered to the patient's skin above the sternum.

8. The device according to claim 7, in which the one or more arcuate bands exert a force on the patient's skin adhered to the one or more arcuate bands during the release of the chest wherein the vector of the force deviates from an anterior-posterior axis of the patient's chest.

9. The device according to claim 8, in which the vector of the force deviates from the anterior-posterior axis by more than 5 degrees in the superior direction along a superior-inferior axis of the chest to aid a pump-handle motion of the chest.

10. The device according to claim 8, in which the vector of the force deviates from the anterior-posterior axis by more than 5 degrees in a lateral direction.

11. The device according to claim 1, in which the one or more arcuate bands are configured to be adhered to the patient's skin lateral to the sternum.

12. The device according to claim 11 in which the one or more arcuate bands exert a force on the patient's skin adhered to one or more resilient portions during the release of the chest wherein the vector of the force deviates from an anterior-posterior axis of the patient's chest.

13. The device according to claim 12, in which the vector of the force deviates from the anterior-posterior axis by more than 5 degrees in a lateral direction.

14. The device according to claim 12, in which the vector of the force deviates from the anterior-posterior axis by more than 5 degrees in the superior direction along a superior-inferior axis of the chest to aid a pump-handle motion of the chest.

15. The device according to claim 1, in which the one or more arcuate bands comprise the inner surface configured to contact the patient's skin that is coated with an adhesive suitable for adhering to the patient's skin.

16. The device according to claim 15, in which the adhesive covers substantially an entire inner surface configured to contact the patient's skin.

17. The device according to claim 15, in which the adhesive is an adhesive gel.

18. The device according to claim 15, in which the adhesive is an adhesive tape.

19. The device according to claim 1, in which the one or more arcuate bands comprise the inner surface configured to contact the patient's skin having one or more suction cups for adhering to the patient's skin.

20. The device according to claim 19, in which the one or more suction cups are located over substantially an entire inner surface configured to contact the patient's skin.

21. The device according to claim 1, in which the one or more arcuate bands are dimensioned to fit at least partially around the chest of the patient.

22. The device according to claim 21, in which the one or more arcuate bands comprise one or more springs.

23. The device according to claim 1, comprising the one or more arcuate bands joined to a central portion, with the one or more arcuate bands extending from opposite sides of the central portion, such that, when the central portion is disposed under the patient, the one or more arcuate bands extend at least partially around the chest of the patient.

24. The device according to claim 23, in which the central portion is constructed from a resilient material.

25. The device according to claim 23, in which the central portion is constructed from a rigid material.

26. The device according to claim 23, in which the one or more arcuate bands are between 3 and 6 inches in width.

27. The device according to claim 1, in which the one or more arcuate bands are configured to be secured around the patient's chest by one or more straps.

28. The device according to claim 27, in which the one or more straps are attached to the one or more arcuate bands at or near an anterior end of the one or more arcuate bands.

29. The device according to claim 1, in which the one or more arcuate bands are between approximately 12 and 24 inches in length.

30. The device according to claim 1, wherein the one or more arcuate bands consist of one arcuate band that is between approximately 12 to 36 inches in length.

31. The device according to claim 30, wherein the one arcuate band is approximately 3 to 6 inches wide.

32. The device according to claim 1, wherein posterior ends of two arcuate bands of the one or more arcuate bands are joined to a spring.

33. The device according to claim 32, wherein the spring is a flat spring.

* * * * *